United States Patent [19]

Damico et al.

[11] Patent Number: 4,668,230
[45] Date of Patent: May 26, 1987

[54] BOWED, TROUGH-LIKE ABSORBENT PAD

[75] Inventors: Joyce A. Damico; Rebecca J. Weber, both of Winnebago County; James J. O'Connor, Calumet County, all of Wis.

[73] Assignee: Kimberly-Clark Corporation, Neenah, Wis.

[21] Appl. No.: 629,297

[22] Filed: Jul. 9, 1984

[51] Int. Cl.$^4$ ............................................. A61F 13/16
[52] U.S. Cl. ................................................. 604/385 A
[58] Field of Search .............. 604/385, 358, 367, 374, 604/371, 372, 375

[56] References Cited

U.S. PATENT DOCUMENTS

| | | |
|---|---|---|
| 2,273,542 | 2/1942 | Tasker . |
| 3,371,668 | 3/1968 | Johnson . |
| 3,570,493 | 3/1971 | Olsson .................... 604/372 |
| 4,050,462 | 9/1977 | Woon et al. . |
| 4,182,334 | 1/1980 | Johnson . |
| 4,226,238 | 10/1980 | Bianco . |
| 4,253,461 | 3/1981 | Strickland et al. . |
| 4,315,508 | 2/1982 | Bolick . |
| 4,319,572 | 3/1982 | Widlund et al. ............ 604/385.2 |
| 4,324,245 | 4/1982 | Mesek et al. . |
| 4,326,528 | 4/1982 | Ryan et al. .................. 604/385 A |
| 4,333,782 | 6/1982 | Pieniak ........................... 156/164 |
| 4,337,771 | 7/1982 | Pieniak et al. . |
| 4,490,148 | 12/1984 | Beckestrom ............... 604/385 A |
| 4,496,360 | 1/1985 | Joffé et al. . |
| 4,555,244 | 11/1985 | Buell ........................... 604/392 |
| 4,579,556 | 4/1986 | McFarland ................ 604/385.2 |

FOREIGN PATENT DOCUMENTS

| | | |
|---|---|---|
| 0067916 | 12/1982 | European Pat. Off. . |
| 0091412 | 10/1983 | European Pat. Off. . |
| 0098512 | 1/1984 | European Pat. Off. . |
| 0155515 | 9/1985 | European Pat. Off. . |
| 1815857 | 8/1969 | Fed. Rep. of Germany . |
| 1554865 | 10/1979 | United Kingdom . |
| 2142241 | 1/1985 | United Kingdom . |
| 2142242 | 1/1985 | United Kingdom . |
| 2142541 | 1/1985 | United Kingdom . |

Primary Examiner—John D. Yasko
Attorney, Agent, or Firm—Paul A. Leipold; Donald L. Traut; Jeremiah J. Duggan

[57] ABSTRACT

The pad of the invention is composed of impervious backing sheet and a pervious body-side liner with an absorbent material there between. The pad is elasticized along its edges from points at substantially one end extending along the longer edges of the rectangular pad for at least two-thirds of the length of the pad. In a preferred form of the invention the pad has as its absorbent material a coform structure of air-formed melt-blown polymers combined with air-formed cellulose fibers that have been formed onto a pervious spun-bonded material that serves as the pervious body-side liner. In the preferred form the backing sheet is formed of an extrusion-coated spunbonded material that has the spunbonded material on the outer surface with the backing sheet folded over to overlap on the body side of the garment with the fabric toward the body. The folded portion forms the pad's baffles. Further, the preferred pad has length of between about 8 and 14 inches, and the width is preferably about 30 percent of the length.

20 Claims, 6 Drawing Figures

BOWED, TROUGH-LIKE ABSORBENT PAD

TECHNICAL FIELD

The invention relates to an improved disposable absorbent garment intended to be used to receive discharge from the body. The proposed pad may be used for absorption of bodily exudate such as menstrual fluid or urine.

BACKGROUND

Many articles used as incontinent products or menstrual pads have been found unsatisfactory as they are bulky and/or ineffective. Many such garments are formed by forming flat sheets into a diaper-like structure for incontinent use. Other pads for catamenial use have been formed in thin flat structures, but these structures have been low in absorption. Further, flat structures have a tendency to wrinkle between the legs during use causing discomfort and distorting the target area where the exudate will be located.

Small elasticized pads have been proposed, such as in U.S. Pat. No. 3,371,668, to Johnson in which an elasticized sanitary napkin is disclosed. The sanitary napkin has elastic threads that are imbedded in the napkin, running in the long direction of the napkin. Another small elasticized pad has been proposed in European Patent application No. 0,091,412, of Nedestam in which a sanitary napkin having elasticized edges and a raised center portion is disclosed. However, these pads have not found wide acceptance as they are bulky and do not fit the female form to provide both comfort and absorbency.

It has been known in the diaper art to provide diapers that are shaped by having elastic at the edges. Such diapers have been disclosed in U.S. Pat. No. 4,333,782 of Pieniak and U.S. Pat. No. 4,050,462 to Woon et al. However, diaper-like structures are not suitable for use as a catamenial napkin, or for use as a absorbent member for an adult with a mild urinary incontinent problem. They are too large, bulky, and obtrusive to be suitable for such use.

Therefore, there remains a need for a napkin for catamenial and urinary incontinence use for women that will not bunch during walking and is comfortable.

DISCLOSURE OF THE INVENTION

An object of this invention is to provide a comfortable, incontinence and catamenial pad.

A further object of this invention is to provide a low cost shaped incontinence and catamenial pad.

An additional object of the invention is to provide a discreet, highly-absorbent, nonleaking urinary incontinent pad.

These and other objects of the invention are generally accomplished by providing a pad that is composed of an impervious backing sheet and a pervious body-side liner with an absorbent material there between. The pad of the invention is elasticized along its edges from points substantially at one end extending along the longer edges of the rectangular pad for at least two-thirds of the length of the pad.

In a preferred form of the invention the pad has as its absorbent material a coform structure of air-formed meltblown polymers combined with air-formed cellulose fibers that have been formed on a pervious spunbonded material that serves as the pervious body-side liner. In the preferred form the backing sheet is formed of an extrusion-coated spunbonded material that has the spunbond material on the outer surface with the backing sheet folded over to overlap on the body side with the fabric toward the body forming the pad's baffles. Further, the preferred pad has a length of between about 80 to 90 percent of about 8 and 14 inches and the width is preferably about 30 percent of the stretched length.

MODES FOR CARRYING OUT THE INVENTION

The invention has numerous advantages over the prior incontinent pads and previous catamenial pads. The pad of the invention is comfortable. The pad of the invention also will have less tendency to crease and be distorted when it is worn. Therefore, it will remain in the target area and therefore is less likely to leak. Further, previous garments for mild urinary incontinence were bulky, unsightly, and had a greater tendency to leak. The pad of the invention is also somewhat easier to form in that folding of the device is not necessary and attachment and suspension devices are not necessary or are very simple. These and other advantages of the invention will become apparent from the description below.

Figure 1:
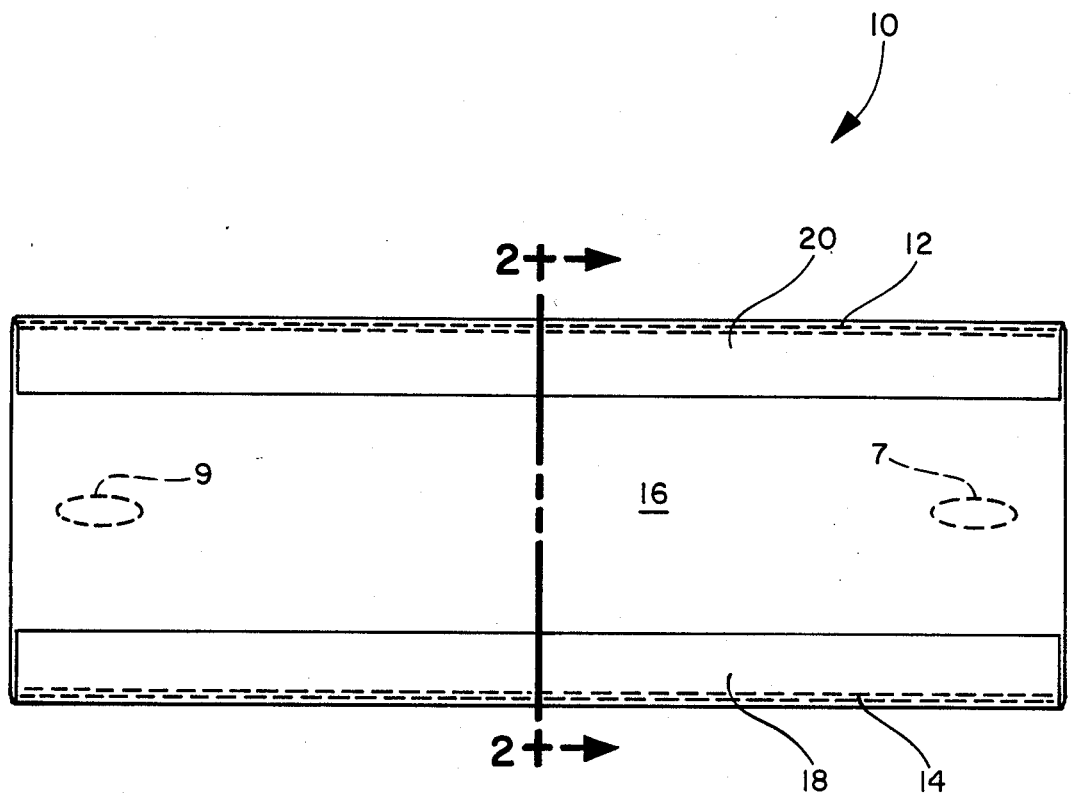
FIG. 1 is a plan view of a garment in accordance with the invention in extended condition with the body contacting portion toward the viewer.
Figure 2:
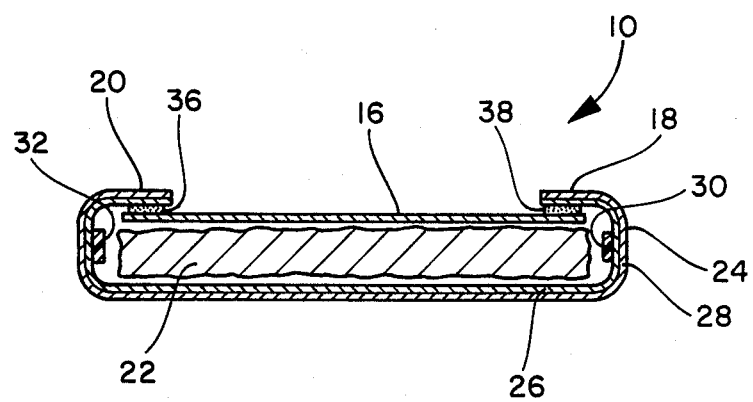
FIG. 2 is a cross section of FIG. 1 along line 2—2.

FIG. 1 illustrates a pad in accordance with the invention in extended position. The pad has elasticized areas 12 and 14 extending along substantially the entire length of the longer sides of the rectangular pad 10. The pad has a pervious liner material 16. The impervious backing, not visible, is folded over to form baffles 18 and 20 on the body side of pad 10. The cross-sectional view of FIG. 2 shows the baffles 18 and 20 overlapping the pervious body side liner 16. The backing sheet 24 is composed of a fabric layer 28 that is on the outer surface and an inner impervious layer 26 from an integral sheet. The baffles 18 and 20 are adhesively connected to the pervious sheet 16 at 36 and 38. The cloth-like outer surface 28 of the baffles 18 and 20 is particularly desirable as the baffles will be in contact with the skin and the cloth-like outer surface will be less likely to cause abrasion, skin reddening and other irritation to discomfort the wearer. The pad has an interior absorbent 22 that is surrounded by the impervious member 24 at the sides and back. The elastic members 30 and 32 serve to gather the elasticized edges of the garment and cause it to assume the trough-like configuration.

Figure 3:
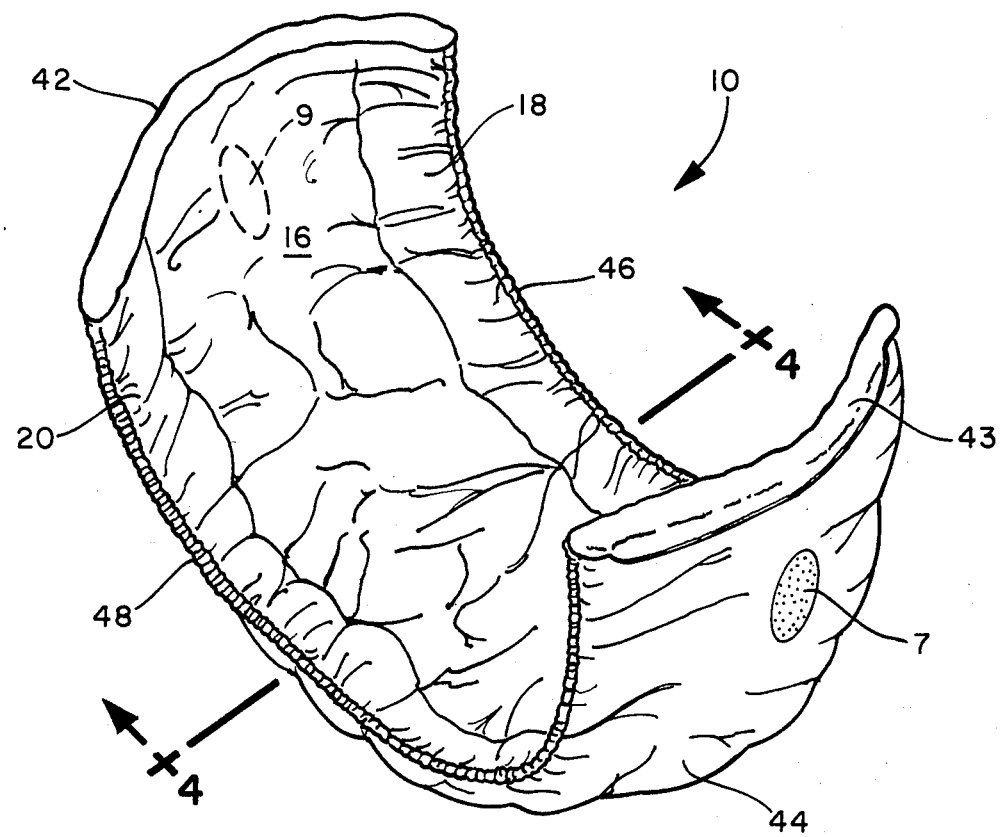
FIG. 3 is a view of a pad in accordance with the invention.

As illustrated in FIG. 3 the garment will, when the elastic is relaxed, assume a bowed, trough-like configuration with upturned ends 40 and 42. The bottom 44 of the trough will be about one inch below the sides of the trough 46 and 48. As is apparent from FIG. 3 the bowed trough-like shape will readily conform to the public area of a woman. Further, when it is thus conformed it will not have a tendency to wrinkle in the middle so as to distort target area. Further, as the pad 10 assumes a trough-like configuration, the depressed center portion will not have a tendency to contact and irritate the vulva or other sensitive portions of the perineal region of the wearer. Further, while described primarily as a woman's product, it is apparent that in the larger sizes that it is suitable for use by a male for light-to-moderate urinary incontinence problems.

As is apparent from FIGS. 1 through 3, the device also may be formed from four simple rectangular pieces of material. The impervious liner, absorbent member, and outer sheet that forms the backing and baffles are all rectangular. Further, the elastic is placed onto the garment in straight lines for the entire distance, thereby simplifying the control of the adhesion of the elastic to the garment. The intermittent adhesion of elastics to diapers and other incontinent garments has been a complicating factor in their manufacture and continuous adhesion is a manufacturing advantage. Further, the production of a garment that does not require folding after formation may also be an advantage. The garments of the invention nest very well to form stacks for shipping, boxing, and storing.

Figure 4:
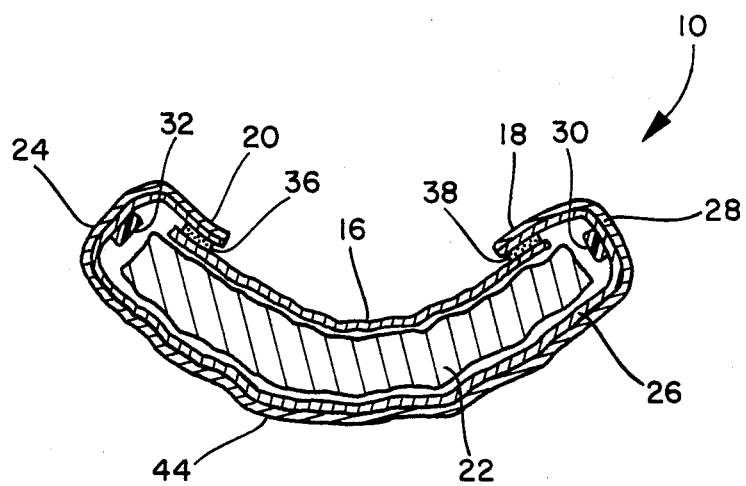
FIG. 4 is a cross section along line 4—4 of FIG. 3.

FIG. 4 is a cross section along line 44 of FIG. 3 illustrating the trough-like configuration of the garment 10. When in relaxed configuration the garment forms a trough-like structure at the bottom 44.

Figure 5:
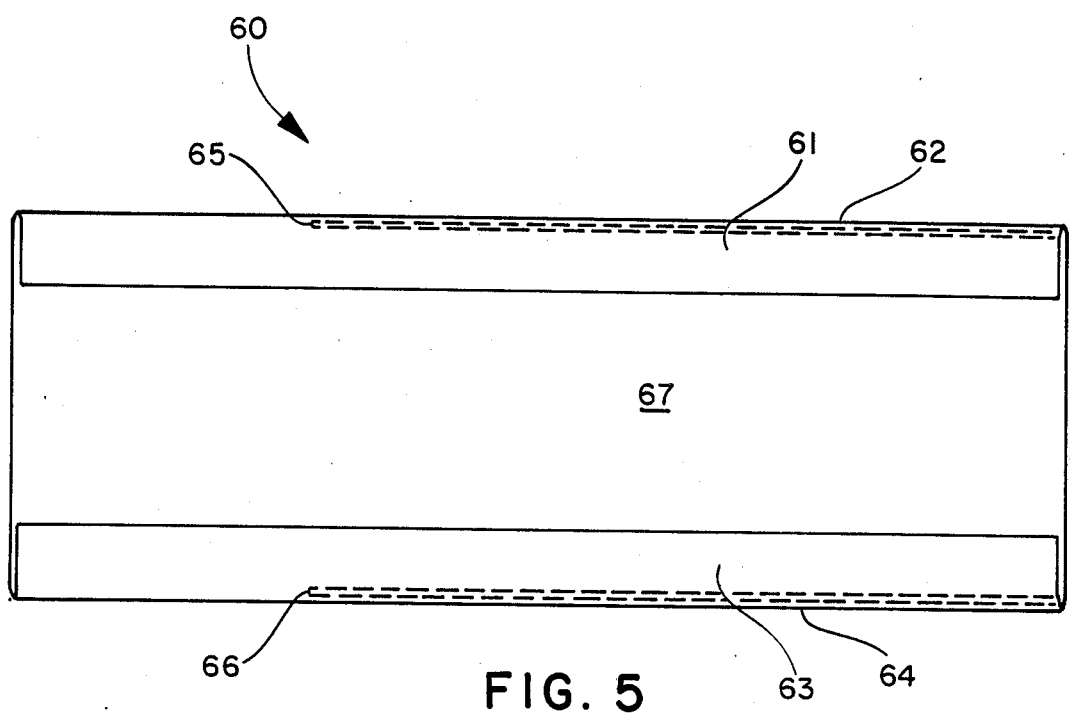
FIG. 5 is a plan view of a alternate pad in accordance with the invention.
Figure 6:
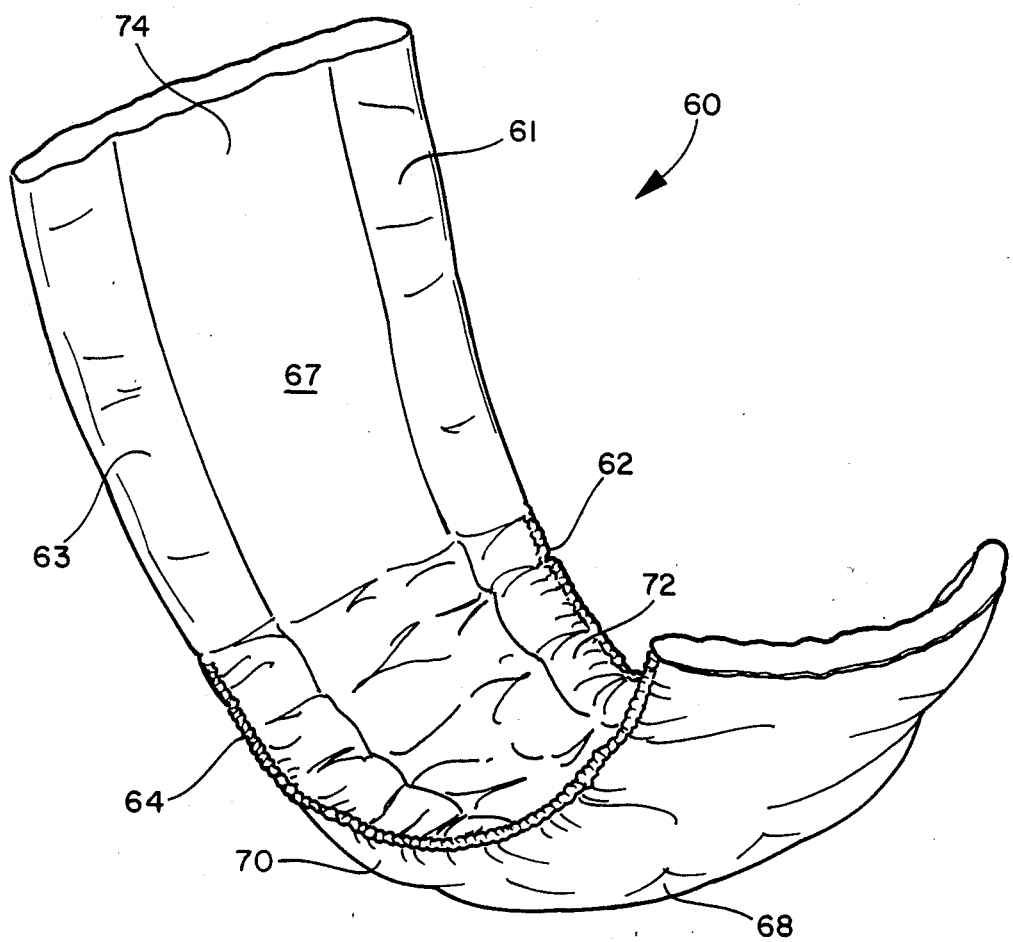
FIG. 6 is a perspective view of the pad of FIG. 5 in relaxed condition.

FIGS. 5 and 6 illustrate an alternate garment formed in accordance with the convention. The garment of FIG. 5 viewed in extended condition has elastic 62 and 64 extending substantially from one end of pad 60 to points 66 and 65 about two-thirds of the way toward the other end. These elastics as viewed in FIG. 6 cause the pad 60 to assume a configuration in the relaxed position generally corresponding to a "j." The "j" pad has a lower portion having a trough-like configuration with a bottom 68 and sides 70 and 72. The pad also has baffles 61 and 63 to aid in the prevention of leaking from the sides of the pad. The nonelasticized part 74 may be worn towards the back of the garment over the buttocks to aid in prevention of leaking of the garment in use. The nonelastized parts 74 will make less likely the leaking of urine when the wearer is seated. The "j"-shaped garment has the advantage that the elasticized trough-like portion 68 will conform to the perineal area and not be deformed in such a manner to cause leaking during movement of the wearer. The nonelastized portion 74 extends upward and aids in holding of the device in place while also providing additional absorption capacity and reducing the tendency to leak when the wearer is sitting.

The impervious backing sheet member of the invention may be made of any suitable material that does not allow the passage of aqueous liquids. Typical of such material are sheets of polyethylene, polypropylene and other polymer and copolymer materials. A preferred material is a sheet formed by extrusion of polyethylene onto a spunbonded fabric material. The spunbonded material is formed by spinning of fine continuous filaments of polypropylene onto a moving belt. The coextruded sheet is formed by extrusion of a very thin layer of polyethylene polymer onto the spunbonded fabric. This material is very light in weight and low in cost as the polymer use is quite low. Further, in the preferred construction the backing sheet is folded onto the body side at the edges to form baffles. The baffles being in contact with the skin are more comfortable with the cloth being exposed rather than the polymer sheet. The polymer sheet, without a cloth-like surface, when contacting the skin is more likely to cause reddening, abrasion, and deterioration of the skin. However, the plain polymer sheet could be used if a lower-cost product is desired.

The absorbent material may be any of many well-known absorbents. Typical of such absorbent material is fluff formed of divellicated wood fibers. A preferred absorbent is coform fabric absorbent sheets. Coform is an air-formed combination of divellicated wood fibers and meltblown polymer, normally polypropylene. This material is found to have high integrity and absorbency when present in a thin pad. The formation of coform is disclosed in U.S. Pat. No. 4,100,324 Anderson et al. that is hereby incorporated by reference. The use of a coform material also containing superabsorbent, such as disclosed in UK Patent Pub. No. 2,113,731 of Aug. 10, 1983, is particularly desirable in view of its light-weight and thinness of the superabsorbent containing coform in combination with its very high absorbency.

The garment of the invention may be designed to hold any desired amount of fluid by selection of appropriate amounts and types of absorbents. It is preferred for mild incontinence use that the pad be able to rapidly absorb and retain between about 20 and about 60 cc of aqueous fluid. Mild incontinence, suitable for the use of the pad of the invention, generally refers to those persons having a stress incontinence where quantities of urine may be lost when an activity such as sneezing or laughing is performed and also to those persons with a more or less constant dribble of urine. A pad with the specified absorbency is suitable for such incontinence problems.

The pervious liner material may be of any known materials for absorbent pad use that are nonirritating to the skin of the wearer and will easily pass fluids but not absorb them. Typical of such material are perforated polymer sheets, tissue, and nonwoven fabrics. The preferred material is spunbonded polypropylene fabric sheet. In its most preferred form the spunbonded polypropylene is treated with a wetting agent or surfactant to make it hydrophylic and also is bonded to a coform layer. The bonding may be achieved by adhesive connection, by embossing or ultrasonics, or in a most preferred form the spunbonded polypropylene sheet is used as a forming layer onto which the coform material is applied in an air stream. Adhesion of the covering sheet to the coform aids in transfer of liquid through the sheet to the absorbent. However, the pad of the invention does not require the pervious liner to be bonded to the absorbent material. The pervious liner may be wrapped around the impervious backing material and absorbent or may be glued on top of baffles 18 in some methods of construction of the pad. Bonding of the permeable liner to the absorbent is preferred as it will lower the leakage rate of the pads as urine is less likely to run off.

The generally rectangular elasticized pad of the invention may be of any suitable dimensions. However, it has been found that there are certain dimensions that are preferred in forming a pad that is comfortable and covers enough of the pubic region to adequately absorb fluids and not be subject to displacement during movement. The preferred length of the backing sheet material is a rectangular sheet of a length of between about 8 and 14 inches. The elastic is placed on the sheet with a degree of stretch such that after the elastic is relaxed the finished garment will have a length when gently flattened of between about 80 and about 90 percent of the original length of the sheet prior to application of the elastic or between about 6.4 and about 12.6 inches. The width of the pad generally corresponds to about the width of the absorbent material and is about 30 percent of the original length of the rectangular sheet or between about 2.4 to about 4.2 inches. The particularly preferred pad has an original length of about 10 inches and original absorbent width of about 3 inches. This pad is originally formed from an impervious sheet that is about 4.5 inches wide by about 10 inches long with about three-fourths inch (¾") to be folded over on each edge to form the edges and also form an inside baffle. This size sheet is found to produce a pad that is suitable for mild urinary incontinence or catamenial use for an average-sized woman with comfort and effectiveness.

The placement of the elastic in the pads of the invention generally will be at the sides of the absorbent material as indicated in FIG. 2. However, it is also possible that the elastic could be placed on the body side of the absorbent pad by adhering the adhesive to the underside of the baffles. However, it is believed that the pad is more comfortable if the elastic is on the interior wall of the outermost edge of the backing material as illustrated in FIG. 2. It is also possible that the elastic members may be placed beneath the outer edges of the absorbent material and adhered to the backing material in that area either on the interior or exterior of the pad.

The amount of elastic placed onto the sides of the pad may be any necessary amount that will cause the formation of the pad into the desired bowed trough configuration or the "j" configuration. It is generally necessary for the invention that the elastic be adhered beginning at one end of the pad and extending to a point at least about two-thirds of the way toward the other end creating an effective elasticized area of at least about two-thirds of the opposing long edges of the rectangular pad.

The pad may be held in place by the wearer either by a tight fitting garment or by placing of adhesive lines or areas on the exterior facing of the pad. The adhesive will adhere to the underwear of the wearer. It is also possible that the pad could be held in place by belts or straps. The preferred method is to have the pad held by small areas of adhesive on the ends of the pad such as adhesive areas 7 and 9 of pad 10 of FIG. 1.

While the pad of the invention has been described primarily for catamenial and incontinence uses, the pad also could serve as a bandage or wound dressing. It is considered as particularly well suited for use as a bandage on elbows or knees. The pad if used for a bandage, particularly for the adult knee, may have a somewhat longer length dimension, and a width of less than about 30% of the length. The trough-shaped pad finds utility as a dressing, but the size may need to be varied from the incontinence sizes depending on the use of the dressing.

The foregoing specification and drawings are intended to be illustrative and not exhaustive. Other variations and rearrangements of the pad of the invention are possible without departing from spirit of the invention which is intended to be limited only by the breadth of the claims attached hereto.

We claim:

1. An elongated generally rectangular absorbent mild incontinence or catamenial pad comprising a fluid-impermeable outer cover, a fluid-pervious bodyside cover and an absorbent positioned therebetween, wherein the long edges of said pad are elasticized by stretchable elastic from one end of the pad to a point about two-thirds of the distance to the other end of said pad thereby forming a trough-like shape in the elasticized portion of said pad when said elastic is relaxed and wherein said pad forms a j-shape when the elasticized portion is relaxed.

2. The pad of claim 1 wherein said fluid pervious body-side cover is adhered to the absorbent layer.

3. The pad of claim 1 wherein the trough is about 1 inch deep.

4. The pad of claim 1 wherein said cover comprises a fabric-covered polymer film.

5. The pad of claim 1 wherein the length of said pad when flattened is between about 6.4 and about 12.6 inches.

6. The pad of claim 1 wherein the width of said absorbent layer is between about 2.4 and about 4.2 inches.

7. The pad of claim 1 wherein said pad has an absorption capacity between about 20 and 60 cc of aqueous fluid.

8. The pad of claim 7 wherein its length when pressed flat is between about 80 and 90 percent of about 8 and about 14 inches, and the width is about 30 percent of about 8 to about 14 inches.

9. The pad of claim 1 wherein the absorbent extends to substantially the edge of the pad.

10. The pad of claim 1 wherein the absorbent is a coform material that has stability when wet.

11. The pad of claim 1 wherein said pad is provided with adhesive area for fastening said pad to the undergarment of the wearer.

12. An elongated generally rectangular absorbent mild incontinence or catamenial pad comprising a fluid-impermeable outer cover, a fluid-pervious body-side cover, and an absorbent layer positioned there-between and extending substantially to the edges of the pad, wherein the long edges of said absorbent pad are elasticized in each long edge area extending from at least one end of said pad to a point at least about two-thirds of the distance to the other end thereby forming a trough-like shape conforming to the pubic area in the at least elasticized portion of said pad, wherein said pad's length when pressed flat is between about 80 and 90 percent of about 8 and about 14 inches, and the width is about 30 percent of about 8 to about 14 inches.

13. The pad of claim 12 wherein said fluid pervious body-side cover is adhered to the absorbent layer.

14. The pad of claim 12 wherein the trough is about 1 inch deep.

15. The pad of claim 12 wherein said cover comprises a fabric-covered polymer film.

16. The pad of claim 12 wherein the length of said pad when flattened is between 6.4 and about 12.6 inches.

17. The pad of claim 12 wherein the width of said absorbent layer is between about 2.4 and about 4.2 inches.

18. The pad of claim 12 wherein said pad has an absorption capacity between about 20 and 60 cc of aqueous fluid.

19. The pad of claim 12 wherein said pad has an absorption capacity of up to about 60 cc of aqueous fluid.

20. The pad of claim 12 wherein said elastic extends from substantially said one end to said other end.

* * * * *